United States Patent [19]

Gastaud

[11] 4,033,988
[45] July 5, 1977

[54] DERIVATIVES OF 17α-HYDROXY, 19-NORPREGN-4-ENE-3,20-DIONE

[76] Inventor: Jean Marie Gastaud, 3 avenue du prince pierre, Monte Carlo, Monaco

[22] Filed: June 20, 1975

[21] Appl. No.: 588,959

[30] Foreign Application Priority Data

June 28, 1974 United Kingdom ............ 28882/74

[52] U.S. Cl. .................... 260/397.4; 260/239.55 R
[51] Int. Cl.² ......................................... C07J 1/00
[58] Field of Search ................................ 260/397.4

[56] References Cited

UNITED STATES PATENTS 3,452,008  6/1969  Buzby, Jr. et al. ........... 260/239.57

OTHER PUBLICATIONS

CA. vol. 75 (1971) Pars, 20792m, by Kaneko, Hidehiko et al.

Primary Examiner—Elbert L. Roberts

[57] ABSTRACT

Derivatives of 3,20-diketo-17α-hydroxy-19-norpregnene-4 and their method of preparation is described. These compounds are useful as progestationals, pituitary-suppresants, contraceptives, anti-androgens, anti-estrogens, anti-seborrehoeics and inhibitors of benign prostate hyperplasia.

1 Claim, No Drawings

DERIVATIVES OF 17α-HYDROXY, 19-NORPREGN-4-ENE-3,20-DIONE

This invention relates to a series of compounds derived from 17α-hydroxy,19-norpregn-4-ene,3,20-dione, to their preparation and used in human therapeutics by the oral, perlingual, transcutaneous, rectal or parenteral route. Their uses are progestational, pituitary-suppressing, contraceptive, anti-androgenic, anti-estrogenic, anti-seborrhoeic, and for inhibiting benign prostate hyperplasia.

This series consists in derivatives of the following general formula;

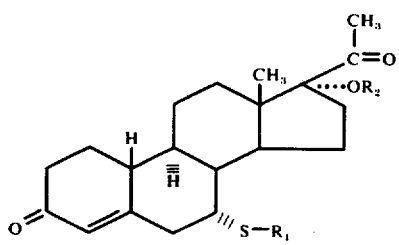
(1)

in which $R_1$ is an acyl or alkyl group, and $R_2$ is either a hydrogen atom or an aliphatic alkyl group containing 1 to 8 carbon atoms, a tetrahydropyranyl residue, or an acyl residue derived from an aliphatic carboxylic acid containing a maximum number of 12 carbon atoms which are either saturated or not. Typical esters are acetate, propionate, oenanthate, t-butylacetate, phenoxyacetate, cyclopentylpropionate, butyrte, pentanoate and hexanoate.

The derivatives defined by general formula (1) are obtained according to the following general pattern:

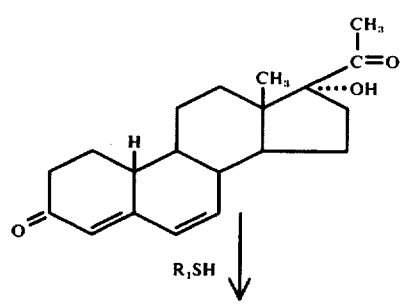
(2)

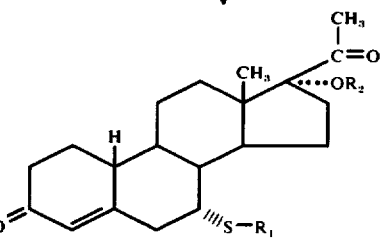

$R_1 = CH_3-CO-$ ;    $R_2 = H$    (4)
$R_1 = CH_3$;    $R_2 = H$    (5)

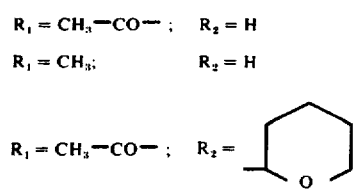

$R_1 = CH_3-CO-$ ;    $R_2 = $    (6)

$R_1 = CH_3$;    $R_2 = $    (7)

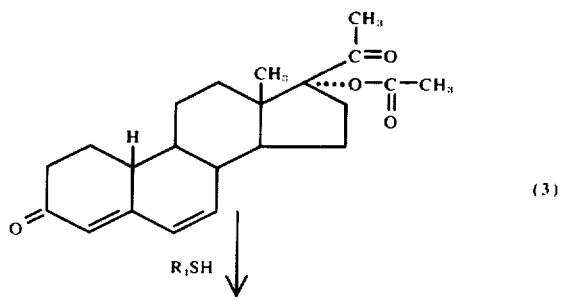
(3)

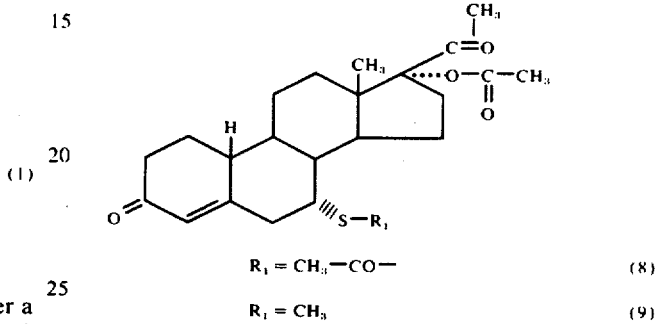

$R_1 = CH_3-CO-$    (8)
$R_1 = CH_3$    (9)

All the derivatives of the series are either prepared from 3,20-diketo-17α-hydroxy-19-norpregnadiene-4,6 (2) (Patents: GER., 1, 130,443, Schering A.G., NETH, 299 968, Syntex Corp.) or from its 17α-acetate (3).

The reagents of the $R_1SH$ type are added to position $C_{7\alpha}$, by condensation, at a temperature varying from 20° to 80° C, in the reagent or in an organic solvent such as benzene, dioxane, or methanol. The reagents used are thioacids such as thioacetic acid or such as $CH_2SH$, $C_2H_5SH$, etc.

The derivatives with a free alcohol function at 17α, e.g. (4) and (5), can be transformed into tetrahydropyranyl ether with dihydropyran in methylene chloride or benzene in the presence of a catalyst such as p-toluenesulphonic acid or phosphorus chloride.

The invention is also concerned with the method of preparation of compounds of general formula (1).

The new derivatives relating to the invention are prepared from 3,20-diketo-17α-hydroxy-19-norpregnadiene-4,6 (2) and 3,20-diketo, 17α-acetoxy-19-norpregnadiene-4,6 (3) which react with thioacetic acid to obtain 3,20-diketo-7α-acetylthio-17α-hydroxy-19-norpregnene-4(4) and 3,20-diketo-7α-acetylthio-17α-acetoxy-19-norpregnene-4 (8) respectively. Derivative 3,20-diketo-7α-acetylthio-17α-hydroxy-19-norpregnene-4 (4) is treated with dihydropyran in the presence of p-toluenesulphonic acid to obtain 3,20-diketo-7α-acetylthio-17α-tetrahydropyranyloxy -19-norpregnene-4 (6). Derivative 3,20-diketo-7α-methylthio-17α-acetoxy-19-norpregnene-4 (9) is obtained from the reaction of methylmercaptan, in an anhydrous dimethylformamide mixture in the presence of sodium methylate, with 3,20-diketo-17α-acetoxy-19-norpregnadiene-4,6 (3).

The following examples illustrate the successive stages of the method as described by the invention.

EXAMPLE NO. 1

3,20-diketo-7α-acetylthio-17α-hydroxy,19-norpregnene-4 (4)

A solution containing 4.7g of $\Delta_6$-19-norprogesterone-17 θOHl (2) and 40cm³ thioacetic acid is maintained at 60° C for 2 hours. After cooling, the solution is diluted with distilled water and neutralised with sodium bicarbonate. After extraction with methylene chloride, a residue is obtained which is then purified by silica column chromatography, in a benzene solution. Derivative (4) is crystallised from methanol.

Melting point: 210°–211° C; centesimal analysis: $C_{22}H_{30}O_4S$.

| N.M.R. spectrum (CDCl$_3$): | | |
|---|---|---|
| H at C$_{(4)}$ | broad singlet | at 348 Hz |
| H at C$_{17\beta}$ | multiplet | at 238 Hz |
| —S—C(=O)—CH$_3$ at C$_{17\alpha}$ | singlet | at 138 Hz |
| —C(=O)—CH$_3$ at C$_{(21)}$ | singlet | at 135 Hz |
| —CH$_3$ at C$_{(18)}$ | singlet | at 45.5 Hz |

Infra-red spectrum (nujol): 1700cm$^{-1}$, 1690, 1660, 1620.

EXAMPLE NO. 2

3,20-diketo-7α-acetylthio-17α-tetrahydropyranyloxy-19-norpregnene-4 (4)

12mg p-toluenesulphonic acid and 0.15cm³ dihydropyran are added to 1.20g of derivative (4) (4) in a solution of 60cm$^{-3}$ methylene chloride. This is then shaken at room temperature and 0.15cm$^{-3}$ dihydropyran are added every half hour for 4 hours. After 6 hours' reaction, the reaction mixture is diluted with an aqueous soltuion of sodium bicarbonate. The organic phase is recovered, washed and distilled. The crude product is purified by silical column chromatography and crystallised from methanol containing 1% pyridine, thus enabling derivative (6) to be isolated.

Melting point: 172° C; centesimal analysis: $C_{27}H_{38}O_5S$
Infra-red spectrum (nujol): 1700cm$^{-1}$, 1680, 1655, 1600, 1100 and 1050.

EXAMPLE NO. 3

3,20-diketo,7α-acetylthio,17α-acetoxy,19-norpregnene-4 (8)

2g of derivative (3) in a solution of 20cm³ of thioacetic acid are heated at 60° C for 24 hours. After cooling, the reaction mixture is diluted with a saturated solution of sodium bicarbonate. After extraction with ether and distillation, a residue is obtained which is purified by silica column chromatography. The pure product obtained is crystallised from methanol.

Melting point: 214° C; centesimal analysis: $C_{24}H_{32}O_5S$

| N.M.R. spectrum (CDCl$_3$): | | |
|---|---|---|
| H at C$_{(4)}$ | broad singlet | at 348 Hz |
| H at C$_{17\beta}$ | multiplet | at 238 Hz |
| —S—C(=O)—CH$_3$ at C$_{17\alpha}$ | singlet | at 140 Hz |
| —O—C(=O)—CH$_3$ at C$_{17\alpha}$ | singlet | at 126 Hz |
| CH$_3$ at C$_{(21)}$ | singlet | at 122 Hz |
| CH$_3$ at C$_{(18)}$ | singlet | at 42 Hz |

Infra-red spectrum (nujol): 1725cm$^{-1}$, 1710, 1690, 1660, 1620, 1250–1275.

EXAMPLE NO. 4

3,20-diketo-7α-methylthio-17α-acetoxy-19-norpregnene-4 (9)

2.7g of derivative (3) are added to 80cm³ anhydrous methanol and 50cm³ dry dimethylformamide in a 250cm³ Woulfe's bottle with a magnetic stirrer, a cooler and a gas-bubbling system. While shaking, 1.85g sodium methylate are added and CH$_3$SH (methylmercaptan) bubbled through for 7 hours. The excess methylmercaptan is eliminated in vacuo and the reaction mixture diluted with ice water. After extration with methylene chloride, a 3g residue is obtained which, after purification by silca column chromatography and crystallisation from ether, yields 0.850 of crystals.

Melting point: 230°–232° C; centesimal analysis: $C_{23}H_{32}O_4S$

| N.M.R. spectrum (CDCl$_3$): | | |
|---|---|---|
| H at C$_{(4)}$ | broad singlet | at 354 Hz |
| H at C$_{17\beta}$ | multiplet | at 180 Hz |
| CH$_3$ at C$_{(21)}$ | singlet | at 127 Hz |
| —S—CH$_3$ at C$_{(21)}$ | singlet | at 124.5 Hz |
| O—C(=O)—CH$_3$ at C$_{17\alpha}$ | singlet | at 122.5 Hz |
| CH$_3$ at C$_{(18)}$ | singlet | at 42.5 Hz |

Infra-red spectrum (nujol): 1730cm$^{1}$, 1710, 1660, 1620, 1325, 1250.

BIOLOGICAL ACTIVITY

As indicated in the introduction of this description, the compounds relating to the invention are useful in therapeutics because of their biological activities which were studied on laboratory animals, as summarised below.

a. The progestational activities were studied in immature, female, New Zealand rabbits weighing approximately 1800 g at the beginning of the progestogen treatment.

After 6 days of a daily s.c. injection of 5 μg estradiol benzoate per animal, the test compound was administered (s.c. or orally) for 5 consecutive days, at the appropriate dose.

The animals were sacrificed on the day following the last administration. After histological preparation of the uteri, the progestational activity was determined according to McPhail's index, from 0 to 4:

0 = no activity,

2 = significant activity, of medium importance,
4 = maximum activity.

As an example, the following table shows the results obtained from several series of tests on laboratory animals with three of the derivatives relating to this invention: compounds (6), (8) and (9).

The progestational effect is equivalent (6) and 3 to 7 times greater than that of progesterone by the subcutaneous route (compounds 9 and 8);

analogous to that of medroxyprogesterone acetate by the oral route (9).

b. The pituitary gonadotrophin-suppressing effects of the compounds relating to the invention were revealed by the parabiosis test (Hall, E., "Methods of Animals Exper.", W. J. Gay (Ed.), vol. II, chapter IV, p.223-248, "Parabiosis", Academic Press, 1965) and the test on the inhibition of compensatory hypertrophy of the remaining ovary in hemicastrated female rats (Petersen, T. L., Edgren, R. A., Jones, R. C., "Steroid-Induced Block of Ovarian Compensatory Hypertrophy in Hemicastrated Female Rats", J. Endocr., 1964, 29:255–262).

c. The anti-androgen activity was first directly demonstrated by the test on chick's comb (Dorfman, R. I., "Anti-Androgenic Substances" in "Methods in Hormone Research", Dorfman R. I. (Ed.), Vol. II, chapter VII, "Bioassay", Acad., Press, 1962), the growth of which, stimulated by testosterone, is inhibited by the compounds described herein, and then indirectly, by the inhibiting effect on the development of the costovertebral organ of the hamster (Burdick, K. H., Hill, R, "The Topical Effect of the Anti-Androgen Chlormadinone Acetate and Some of Its Effects on the Hamster Costovertebral Organ", J. Dermat. 1970, 82, Suppl. 6: 19–25). The anti-androgen activity of the claimed compounds is, according to the compound and method used, from 1.5 to 10 times greater than that of progesterone.

THERAPEUTIC APPLICATIONS

The compounds relating to the invention are useful in human therapeutics as progestationals, contraceptives, pituitary-inhibitors, anti-andro gens, anti-estrogens, anti-seborrhoeics and inhibitors of benign prostate tumours.

According to the therapeutic aim, the clinical history and the physico-chemical peculiarities of each of the compounds related to this invention, the latter are administered by one of the following routes: intramuscular, oral perlingual, percutaneous, rectal or vaginal.

The following are four types of examples of appropriate therapeutical preparations.

1. Injectable ampoules containing 100 to 250 mg/ml of compounds: (4, or one of its fatty acid esters formed with 4 to 12 carbon atoms), (6), (7), (8), (9), for instance, in a pharmaceutically acceptable solvent, would be used for contraception or the intra-muscular treatment of: luteal insufficiency during the menstrual cycle, menometrorrhagia, uterine fibromyoma, or prostate hypertrophy. The dosage is to be adapted to each of the above indications; it could vary from 100mg to 2g per treatment or per month.

2. Tablets or soft capsules destined for the oral or perlingual routes, with an appropriate and pharmaceutically acceptable excipient and containing 10 to 30 mg of compound (9), for instance, would be administered for the same indications as above, at a daily dose varying from 10 to 100 mg.

3. Rectal or vaginal suppositories containing from 20 to 50 mg of compounds; (4, or one of its fatty acid esters formed with 4 to 12 carbon atoms), (6), (7), (8), (9) for instance, would be more appropriate for the rectal treatment of prostate hypertrophy or for uterine fibromyomas. The dosage would be between 20 and 50 mg per day.

4. Solutions, emulsions, gels, creams or ointments containing per ml or per gram from 5 to 25 mg of one of compounds (4), (5) or (6), for instance, in a pharmaceutically acceptable excipient, would be destined for the local transcutaneous treatment of seborrhoea (simple or complicated with acne) at a dosage varying from 5 to 25 mg per day.

I claim:
1. 3,20-Diketo-7α-acetylthio-17α-acetoxy-19-norpregnene-4.

* * * * *